(12) United States Patent
Lieberman

(10) Patent No.: US 7,674,266 B2
(45) Date of Patent: Mar. 9, 2010

(54) APPARATUS FOR CUTTING BONE

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 489 days.

(21) Appl. No.: 10/540,381

(22) PCT Filed: Dec. 23, 2003

(86) PCT No.: PCT/US03/41043

§ 371 (c)(1),
(2), (4) Date: Jun. 23, 2005

(87) PCT Pub. No.: WO2004/060170

PCT Pub. Date: Jul. 22, 2004

(65) Prior Publication Data

US 2006/0074426 A1  Apr. 6, 2006

Related U.S. Application Data

(60) Provisional application No. 60/436,867, filed on Dec. 27, 2002.

(51) Int. Cl.
*A61B 17/00* (2006.01)
(52) U.S. Cl. .................................... 606/79; 606/167
(58) Field of Classification Search .................. 606/79, 606/82, 80, 86, 81, 83, 85, 87, 167, 166, 606/160, 170, 180, 183; 30/320, 321, 356, 30/173, 121, 113.1, 304
See application file for complete search history.

(56) References Cited

U.S. PATENT DOCUMENTS

| 117,588 | A | * | 8/1871 | Woods ........................ 7/138 |
| 2,022,954 | A | * | 12/1935 | Cook ........................ 30/123.5 |
| 2,764,814 | A | * | 10/1956 | Jecker ........................ 30/294 |
| 4,026,295 | A | * | 5/1977 | Lieberman ................. 606/167 |
| 4,239,045 | A | | 12/1980 | Schlein |
| 4,881,534 | A | * | 11/1989 | Uhl et al. ..................... 606/84 |
| 4,969,888 | A | | 11/1990 | Scholten et al. |
| 5,108,404 | A | | 4/1992 | Scholten et al. |
| 5,133,719 | A | | 7/1992 | Winston |
| 5,135,528 | A | | 8/1992 | Winston |
| 5,391,169 | A | * | 2/1995 | McGuire ..................... 606/79 |
| 5,443,474 | A | * | 8/1995 | Sfakianos et al. ........... 606/167 |
| 5,507,800 | A | * | 4/1996 | Strickland .................. 606/167 |
| 5,827,311 | A | * | 10/1998 | Berelsman et al. ......... 606/167 |

(Continued)

Primary Examiner—Pedro Philogene
(74) Attorney, Agent, or Firm—Tarolli, Sundheim, Covell & Tummino LLP

(57) ABSTRACT

An apparatus (10) for cutting bone includes a shaft member (12) having a central axis (14) and extending between a proximal end portion (16) and a distal end portion (18). The proximal end portion (16) has a first surface (32) adapted to receive repetitive impacts. The distal end portion (18) includes a cutting blade (40) extending in a first plane between a shield section (46) and a guide portion (60). The shield section (46) and the guide section (60) project axially beyond the cutting blade (40) to recess the cutting blade (40) in the distal end portion (18). The shield section (46) includes an inwardly facing shield surface (48) which extends in a second plane that is transverse to the first plane of the cutting blade (40). The apparatus (10) is a form of an osteotome that is particularly useful for certain spine-related surgical procedures.

9 Claims, 2 Drawing Sheets

U.S. PATENT DOCUMENTS 5,908,433 A * 6/1999 Eager et al. .............. 606/170
6,595,996 B2   7/2003 Dinger et al.
2003/0100905 A1 * 5/2003 Mears .................... 606/81

* cited by examiner

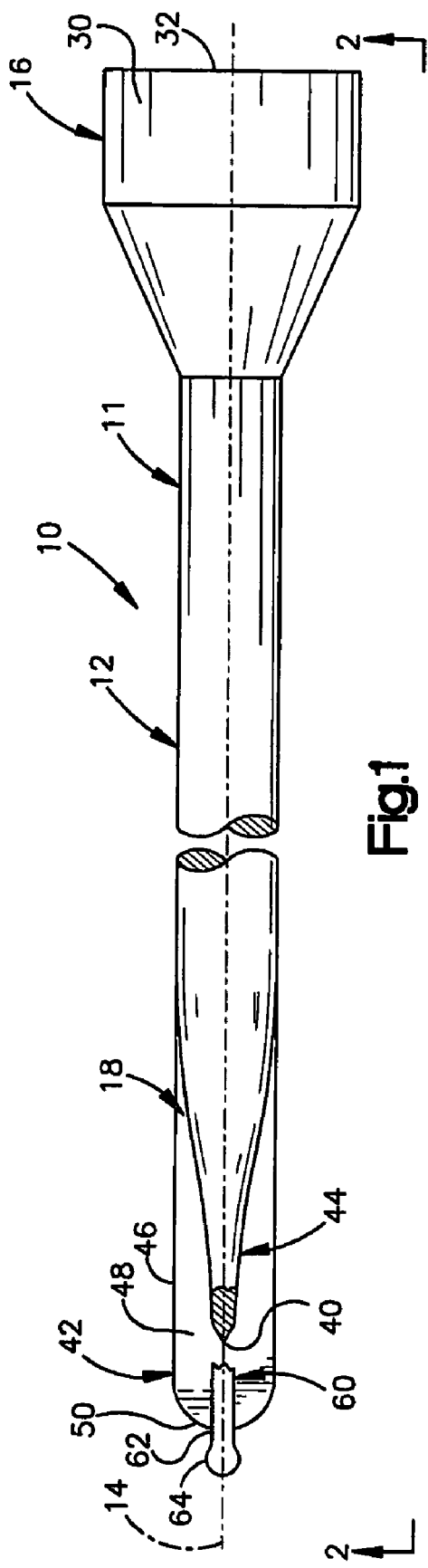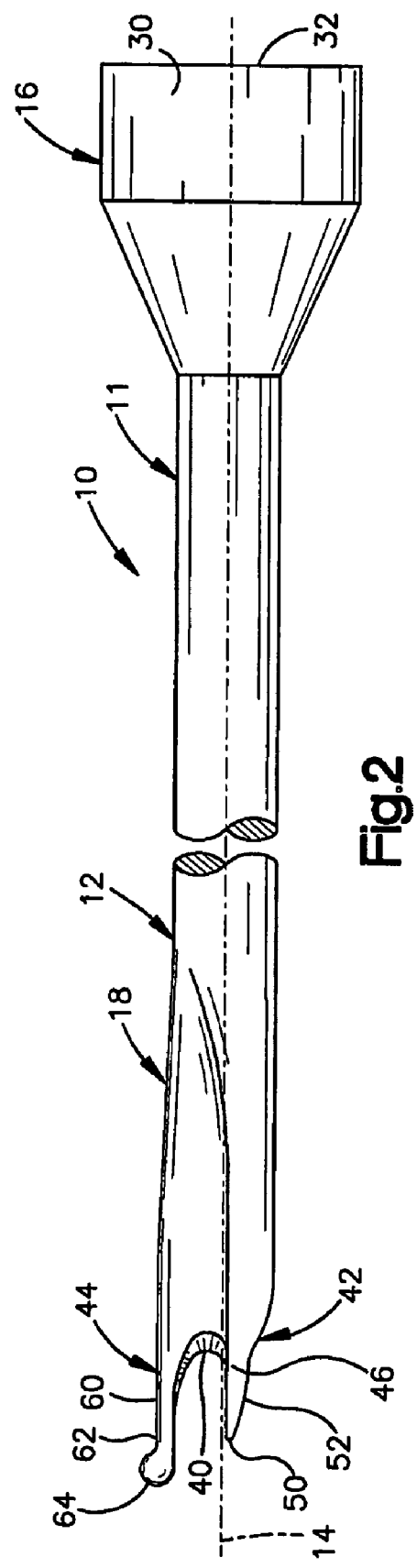

APPARATUS FOR CUTTING BONE

RELATED APPLICATIONS

The present application claims the benefit of U.S. Provisional Patent Application Ser. No. 60/436,867, entitled PERCUTANEOUS CONTROLLED VERTEBRAL OSTEOTOMY TOOL SET, filed Dec. 27, 2002.

TECHNICAL FIELD

The present invention relates to an apparatus for cutting bone and, in particular, is directed to a uniquely designed osteotome that is useful in cutting vertebrae.

BACKGROUND OF THE INVENTION

A known procedure for treating vertebral compression fractures and other bone-related disorders is vertebral augmentation with bone cement. Vertebral augmentation can be performed by the direct injection of liquid cement into the collapsed vertebral body (commonly known as "vertebroplasty"). Vertebral augmentation can also be performed after the restoration of the vertebrae to near normal vertebral body anatomy and creation of an internal cavity with the use of an inflatable bone tamp. This minimally invasive procedure is commonly known as "kyphoplasty" (see, for example, U.S. Pat. Nos. 4,969,888 and 5,108,404). During the kyphoplasty procedure, the inflatable bone tamp is inserted through a small skin incision which accommodates a working tube passed into the vertebral body. Inflation of the bone tamp compresses the cancellous bone and desirably moves the fractured cortical bone to its pre-fractured orientation, creating a cavity within the vertebral body that can then be filled with a settable material such as a cement or any number of synthetic bone substitutes. In effect, the procedure sets the vertebral body at or near its pre-fracture position and creates an internal cast, protecting the vertebral body from further fracture and/or collapse.

As compared to a traditional vertebroplasty procedure, kyphoplasty restores the vertebrae to a pre-fractured condition and the injected bone filler is less likely to leak out of the vertebral body during a kyphoplasty procedure. However, under some circumstances, it has been observed that unpredictable reductions can occur with the kyphoplasty technique in chronic or partially healed collapsed vertebral bodies. Under those circumstances, the surgeon would typically resort to a large, open operation to re-align any post-traumatic kyphosis. Further, inadequate reductions can occur with certain other spinal deformities such as scoliosis and kyphosis using the known techniques and surgical tools. The large, open operations can carry with them significant morbidity in an already physiologically compromised elderly population. The principle benefit of a percutaneous minimally invasive approach, which is the hallmark of the kyphoplasty procedure, is the minimal morbidity associated with the procedure. In this light, additional tools are required to further the kyphoplasty technique, achieve better anatomic re-alignment of the spine, and maintain the minimally invasive nature of the surgery. The additional tools will be deployed through small working portals and be able to achieve the desired strategic vertebral osteotomies to move bone in three dimensional space. One such desirable tool would provide a minimally invasive means to safely cut the lateral (or side) wall of a vertebral body, such as a lateral wall with a prior, and at least partially healed, compression fracture.

SUMMARY OF THE INVENTION

The present invention is an apparatus for cutting bone. The apparatus comprises a shaft member having a central axis and extending between a proximal end portion and a distal end portion. The proximal end portion has a first surface adapted to receive repetitive impacts. The distal end portion includes a cutting blade extending in a first plane between a shield section and a guide section. The shield section and the guide section project axially beyond the cutting blade to recess the cutting blade in the distal end portion. The shield section includes an inwardly facing shield surface which extends in a second plane that is transverse to the first plane of the cutting blade.

The present invention further provides an apparatus for cutting through the cortical bone of a vertebral body, the cortical bone having an outer peripheral surface and an inner surface surrounding cancellous bone. The apparatus comprises an elongate member having a shaft portion extending along a central axis between a proximal end portion and a distal end portion. The proximal end portion has a platform adapted to receive repetitive impacts to advance the elongate member along the vertebral body. The distal end portion of the elongate member includes an arcuate cutting blade extending in a first plane between first and second tip portions. The cutting blade is adapted to cut through the cortical bone of the vertebral body as the elongate member is advanced. The first tip portion has a shield surface which extends in a second plane that is transverse to the first plane of the cutting blade. The shield surface shields the cutting blade to prevent undesired cutting of soft tissues present on the outer peripheral surface of the vertebral body. The second tip portion comprises a blunt tooth extending generally parallel to the central axis and acting as a guide to ensure that the distal end portion of the elongate member follows the contours of the inner surface of the vertebral body as the elongate member is advanced.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a side view of an apparatus for cutting bone constructed in accordance with the present invention;

FIG. 2 is a plan view taken along line 2-2 in FIG. 1;

DESCRIPTION OF EMBODIMENTS

Figure 3:
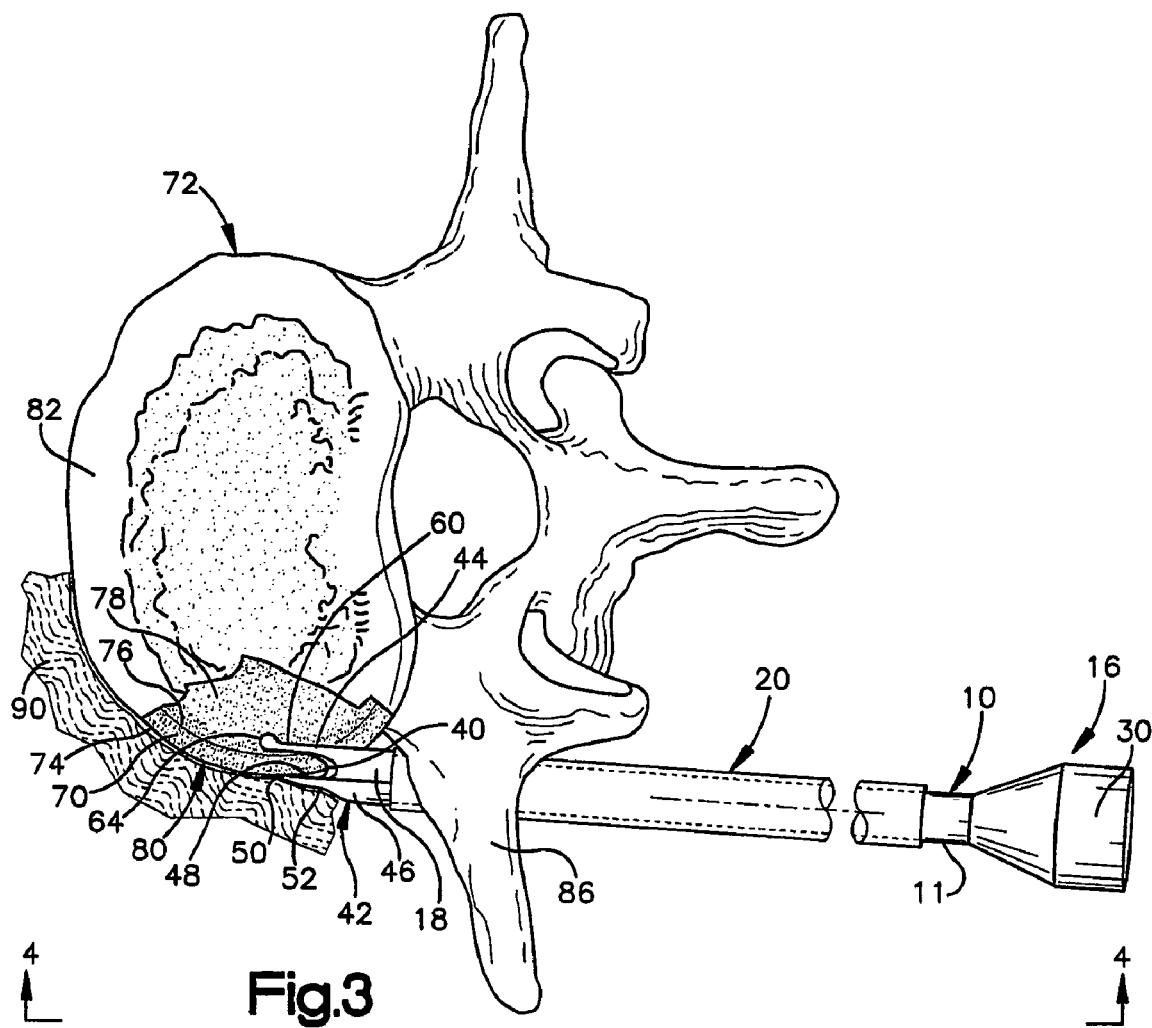
FIG. 3 is a plan view illustrating the apparatus of FIG. 1 being used to cut a lateral wall of a vertebral body.

The present invention relates to an apparatus for cutting bone and, in particular, is directed to a uniquely designed osteotome that is useful in cutting vertebrae. As representative of the present invention, FIGS. 1 and 2 illustrate an apparatus 10 comprising an elongate member 11 made of a medical grade metal such as stainless steel. The elongate member 11 includes a shaft portion 12 extending along a central axis 14 between a proximal end portion 16 and a distal end portion 18 of the apparatus 10. In accordance with one embodiment of the invention, the shaft portion 12 and the distal end portion 18 are designed to fit through a 5 mm (inner diameter) cannula 20 (FIG. 3) and thus have a maximum outer diameter of 4.8 mm. It should, however, be understood that the apparatus 10 and the cannula 20 could have correspondingly larger or smaller diameters.

The proximal end portion 16 of the apparatus 10 has a platform 30 with a planar surface 32 adapted to receive repetitive impacts from another tool, such as a hammer (not shown), to advance the elongate member 11. The platform 30 has a larger outer diameter than the shaft and distal end portions 12 and 18 of the apparatus 10 to facilitate receiving impacts with a hammer.

The distal end portion 18 of the apparatus 10 includes an arcuate cutting blade 40 (FIG. 2) extending in a first plane between first and second tip portions 42 and 44. The cutting blade 40 is recessed axially from the terminal ends of the tip portions 42 and 44 and is adapted to cut through cortical bone as the elongate member 11 is advanced. The first tip portion 42 comprises a shield section 46 having a shield surface 48 (FIG. 1). The shield surface 48 extends in a second plane that is transverse to the first plane of the cutting blade 40. In the embodiment of FIGS. 1 and 2, the shield surface 48 is perpendicular to the cutting blade 40. As may be seen in FIG. 1, the shield section 46 at the distal end portion 18 is approximately the same width (or diameter) as the shaft portion 12 of the apparatus 10. The shield section 46 further includes an arcuate end surface 50 and an outwardly facing ramp surface 52 (FIG. 2). It is contemplated that the end surface 50 could also be sharp similar to a periosteal elevator.

The second tip portion 44 comprises a guide section 60 that extends generally parallel to the central axis 14. The guide section 60 includes a blunt tooth 62 with a bulbous terminal end 64. As may be seen in FIG. 1, the guide section 60 is substantially narrower in width (or diameter) than the shield section 46 and projects axially beyond the end surface 50 of the shield section.

Figure 4:
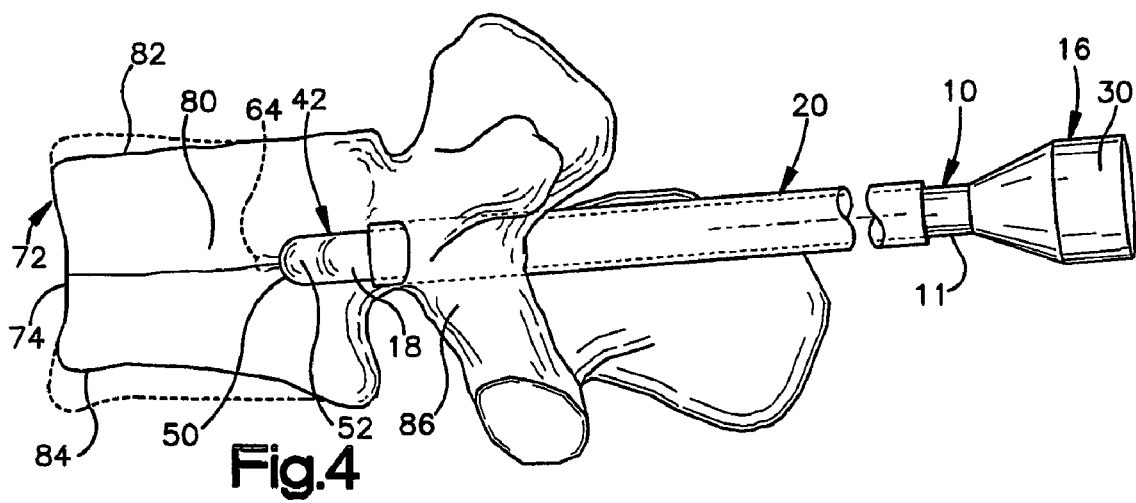
FIG. 4 is a side view taken along line 4-4 in FIG. 3, with soft tissues on the outside of the vertebral body omitted for clarity.

FIGS. 3 and 4 illustrate use of the apparatus 10 to cut bone. Specifically, FIGS. 3 and 4 illustrate the apparatus 10 cutting through cortical bone 70 of a vertebral body 72. The cortical bone 70 of the vertebral body 72 has an outer peripheral surface 74 and an inner surface 76 that surrounds cancellous bone 78. As best seen in FIG. 4, the vertebral body 72 has a partially healed compression fracture to be treated via a kyphoplasty procedure. In order to perform the kyphoplasty procedure, the partially healed cortical bone 70 in the lateral wall 80 of the vertebral body 72 must be cut to release the upper and lower end plates 82 and 84 of the vertebral body so that an inflatable bone tamp (not shown) inserted inside the vertebral body can, when inflated, move the upper and lower end plates back to their pre-fractured positions (illustrated in dashed lines in FIG. 4).

Access to the lateral wall 80 of the vertebral body 72 occurs in a minimally invasive manner via the cannula 20. After drilling a passage through a transverse process 86 of the vertebral body 72, the cannula 20 is placed through the transverse process. The distal end portion, 18 of the apparatus 10 is then inserted through the cannula 20 and into engagement with the lateral wall 80 of the vertebral body. Next, the blunt tooth 64 of the guide section 60 is tapped through the cortical bone 70 of the vertebral body 72 so that the cutting blade 40 is positioned to cut the cortical bone as shown in FIG. 3.

From the position of FIG. 3, the distal end portion 18 of the apparatus 10 is advanced along the lateral wall 80 of the vertebral body 72 through impact blows, either by hand, hammer, or other suitable means to the platform 30 at the proximal end portion 16. As the distal end portion 18 advanced, the cutting blade 40 cuts the lateral wall 80 in order to release the end plates 82 and 84 of the vertebral body 72. Significantly, the bulbous terminal end 64 of the guide section 60 follows the contours of the inner surface 76 of the cortical bone 70 and prevents the distal end portion 18 from straying out of engagement with the vertebral body 72 as the distal end portion is advanced.

Furthermore, as the distal end portion 18 of the apparatus 10 is advanced, the shield surface 48 acts as a shield for the cutting blade 40 to prevent undesired cutting of soft tissues 90, such as blood vessels, nerves, and muscles, present on the outer peripheral surface 74 of the vertebral body 72. In addition, as the distal end portion 18 is advanced, the arcuate end surface 50 of the shield section 46 slides underneath the soft tissues 90 on the outer peripheral surface 74 of the vertebral body 72 and cooperates with the ramp surface 52 to lift the soft tissues off of the outer peripheral surface. This geometry at the distal end portion 18 allows the apparatus 10 to safely cut the lateral wall 80 so that a kyphoplasty procedure can be used to treat the compression fracture of the vertebral body 72 in a minimally invasive fashion.

From the above description of the invention, those skilled in the art will perceive improvements, changes and modifications. For example, it should be understood that, depending on the nature of the condition of a given vertebral body, the lateral wall on the opposite side of the vertebral body 72 shown in FIG. 3, or on both sides of the vertebral body, may need to be cut in order to release the end plates of the vertebrae. In such situations, the apparatus 10 would be used in an identical fashion with access through a cannula placed through the other transverse process. Further, it should be understood that the apparatus 10 disclosed herein could be used to cut through other areas of cortical bone in vertebrae, as well as cortical bone in other bones in a mammalian body. Such improvements, changes and modifications within the skill of the art are intended to be covered by the appended claims.

Having described the invention, I claim:

1. An apparatus for cutting bone, said apparatus comprising:
   a shaft member extending between a proximal end portion and a distal end portion, said shaft member, proximal end portion and distal end portion extending substantially along a central axis, said proximal end portion having a first surface adapted to receive repetitive impacts, said distal end portion including a cutting blade adapted to cut through the bone and extending in a first plane between a shield section and a guide section that extends axially beyond said shield section, said shield section and said guide section being oppositely disposed about said central axis, said shield section and said guide section projecting axially beyond said cutting blade to recess said cutting blade in said distal end portion, said shield section including an inwardly facing shield surface which extends in a second plane that is transverse to said first plane of said cutting blade, said shield surface being substantially wider in width in said second plane than said guide section, said guide section including an enlarged substantially sphere shaped terminal end.

2. The apparatus of claim 1 wherein said shield section includes an arcuate end surface for sliding underneath soft tissues present on the outer peripheral surface of the bone as said shaft member is advanced, said shield surface functioning as a shield for said cutting blade to prevent undesired cutting of the soft tissues.

3. The apparatus of claim 2 wherein said shield section includes an outwardly facing ramp surface for cooperating with said arcuate end surface to lift the soft tissues off of the outer peripheral surface of the bone as said shaft member is advanced.

4. The apparatus of claim 1 wherein said guide section comprises a blunt tooth extending generally parallel to said central axis and acting as a guide to ensure that said distal end portion of said shaft member follows the contours of the inner cortical surface of the bone as said shaft member is advanced.

5. An apparatus for cutting through the cortical bone of a vertebral body, the cortical bone having an outer peripheral surface and an inner surface surrounding cancellous bone, said apparatus comprising:

an elongate member having a shaft portion extending along a central axis between a proximal end portion and a distal end portion, said proximal end portion having a platform adapted to receive repetitive impacts to advance said elongate member along the vertebral body;

said distal end portion of said elongate member including an arcuate cutting blade extending in a first plane between a first tip portion and a second tip portion that extends axially beyond the first tip portion, said cutting blade is adapted to cut through the cortical bone of the vertebral body as said elongate member is advanced;

said first tip portion having a shield surface which extends in a second plane that is transverse to said first plane of said cutting blade, said shield surface for shielding said cutting blade to prevent undesired cutting of soft tissues present on the outer peripheral surface of the vertebral body;

said second tip portion comprising a blunt tooth extending generally parallel to said central axis, said blunt tooth having an enlarged substantially sphere shaped terminal end and acting as a guide to ensure that said distal end portion of said elongate member follows the contours of the inner surface of the vertebral body as said elongate member is advanced, said shield surface of said first tip portion being substantially wider in width in said second plane than said blunt tooth.

6. The apparatus of claim 5 wherein said first tip portion includes an arcuate end surface for sliding underneath the soft tissues on the outer peripheral surface of the vertebral body as said elongate member is advanced.

7. The apparatus of claim 6 wherein said first tip portion further includes an outwardly facing ramp surface for cooperating with said arcuate end surface to lift the soft tissues off of the outer peripheral surface of the vertebral body as said shaft member is advanced.

8. The apparatus of claim 5 wherein said first and second tip portions projecting axially beyond said cutting blade to recess said cutting blade in said distal end portion.

9. An apparatus for cutting bone, said apparatus comprising:

a shaft member having a central axis and extending between a proximal end portion and a distal end portion, said proximal end portion having a first surface adapted to receive repetitive impacts, said distal end portion including a cutting blade extending in a first plane between a shield section and a guide section, said cutting blade being adapted to cut through the bone, said shield section and said guide section being oppositely disposed about said central axis, said shield section and said guide section projecting axially beyond said cutting blade to recess said cutting blade in said distal end portion, said shield section including an inwardly facing shield surface which extends in a second plane that is transverse to said first plane of said cutting blade, said shield surface being substantially wider in width in said second plane than said guide section, said guide section projecting axially beyond said shield section.

* * * * *